US00PP25219P2

(12) United States Plant Patent
Williams

(10) Patent No.: US PP25,219 P2
(45) Date of Patent: Jan. 6, 2015

(54) ***COLOCASIA* PLANT NAMED 'NOBLE GIGANTE'**

(50) Latin Name: ***Colocasia* hybrid**
Varietal Denomination: Noble Gigante

(71) Applicant: Brian Paul Williams, Louisville, KY (US)

(72) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 51 days.

(21) Appl. No.: 13/986,907

(22) Filed: Jun. 17, 2013

(51) Int. Cl.
*A01H 5/00* (2006.01)

(52) U.S. Cl.
USPC ..... Plt./373

(58) Field of Classification Search
USPC ..... Plt./373, 263.1
See application file for complete search history.

*Primary Examiner* — Kent L Bell
(74) *Attorney, Agent, or Firm* — Penny J. Aguirre

(57) ABSTRACT

A new cultivar of *Colocasia* plant named 'Noble Gigante', that is characterized by its large plants that grow up to 2 m in height, its large leaves up to 1.2 m in length that are held horizontal and are green and suffused with purple when young and mature to deep purple, its petioles that are deep purple in color, its inflorescences that are purple in color and sterile, and its vigorous growth habit.

2 Drawing Sheets

Botanical classification: *Colocasia* hybrid.
Cultivar designation: 'Noble Gigante'.

BACKGROUND OF THE INVENTION

The present invention, *Colocasia* 'Noble Gigante', relates to a new and distinct interspecific hybrid of *Colocasia*, hereinafter referred to by its cultivar name, 'Noble Gigante'. 'Noble Gigante' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants that are unique with large leaves and vigorous growth habits. 'Noble Gigante' arose from a cross made in July of 2009 between an unnamed plant of a *Colocasia* of hybrid origin from the Inventor's breeding program as the female parent and an unnamed plant of *Colocasia-gigantea* as the male parent. 'Noble Gigante' was selected as a single unique plant in June of 2010 from amongst the seedlings derived from the above cross.

Asexual propagation of the new cultivar was first accomplished by in vitro propagation under the direction of the Inventor in Eustis, Fla. in May of 2012. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Noble Gigante' as a new and unique cultivar of *Colocasia*.

1. 'Noble Gigante' exhibits large plants that grow up to 2 m in height.
2. 'Noble Gigante' exhibits large leaves up to 1.2 m in length, which are held horizontally.

3. 'Noble Gigante' exhibits leaves that are green and suffused with purple when young and mature to deep purple in color.
4. 'Noble Gigante' exhibits petioles that are deep purple in color.
5. 'Noble Gigante' exhibits inflorescences that are purple in color and sterile.
6. 'Noble Gigante' exhibits a vigorous growth habit.

The female parent of 'Noble Gigante', an unnamed plant of *Colocasia* of hybrid origin, differs from 'Noble Gigante' in being shorter in height, in having smaller leaves that are held vertically, and in producing stolons (no stolons are produced with 'Noble Gigante'). The male parent of 'Noble Gigante', an unnamed plant of *Colocasia gigantea*, differs from 'Noble Gigante' in being taller in height, in having green leaves and in having white inflorescences that are fertile. 'Noble Gigante' can be most closely compared to the *Colocasia esculenta* cultivars 'Black Magic' (not patented) and 'Illustris' (not patented). Both are similar to 'Noble Gigante' in having large leaves that have dark coloration. 'Black Magic' differs from 'Noble Gigante' in being shorter in height, in having leaves that are black in color and held vertically, and in having fertile inflorescences. 'Illustris' differs from 'Noble Gigante' in being shorter in height and in having leaves that are held vertically and green in color and suffused with purple between distinct green veins.

BRIEF DESCRIPTION OF THE DRAWING

The accompanying colored photographs illustrate the overall appearance and distinct characteristics of the new *Colocasia*, 'Noble Gigante'. The photographs were taken of plants about 2 years in age as grown outdoors under 6 mm poly and natural lighting in Louisville, Ky. and planted in a trial garden.

Figure 1:
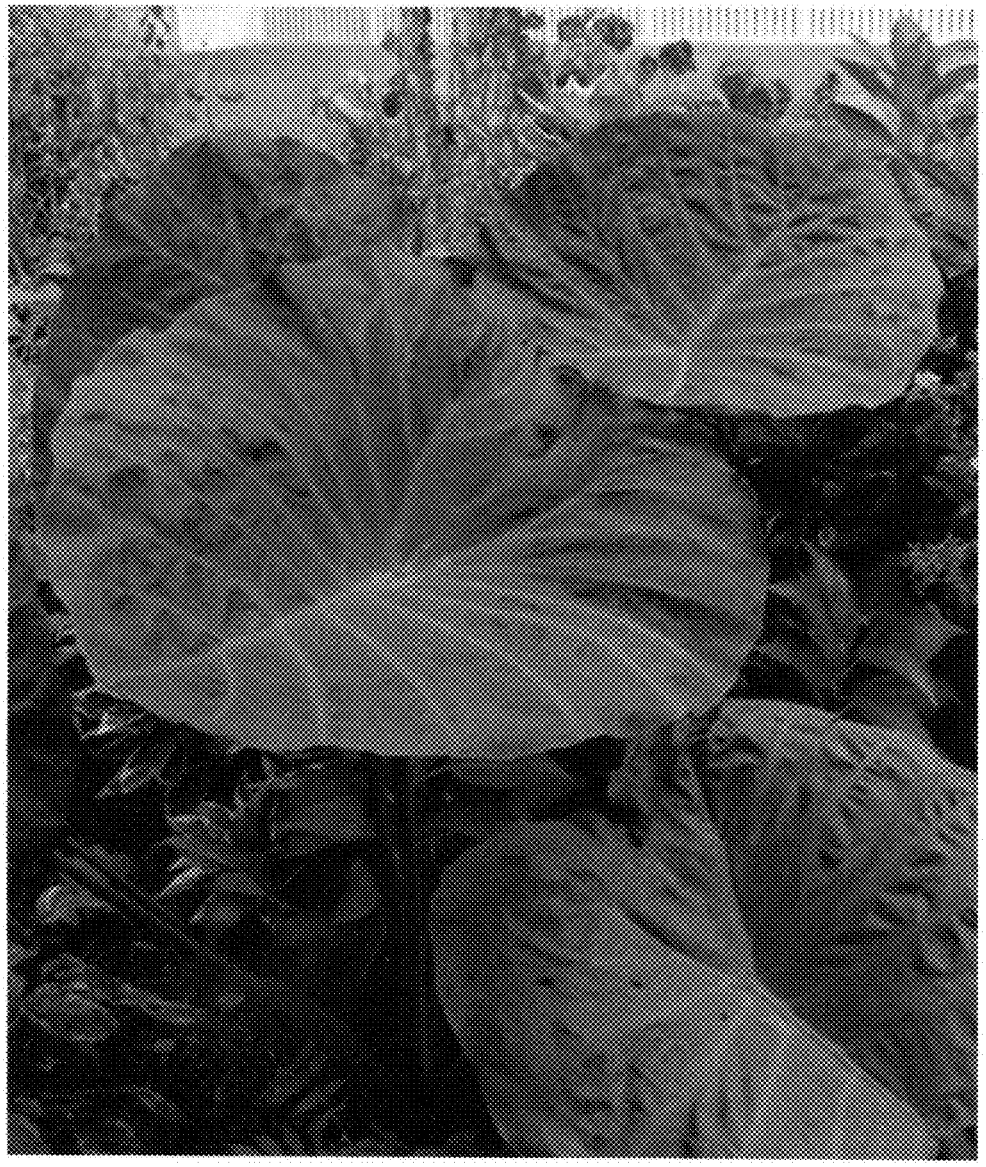
FIG. 1 provides an overall view of the mature foliage and plant habit of 'Noble Gigante'.
Figure 2:
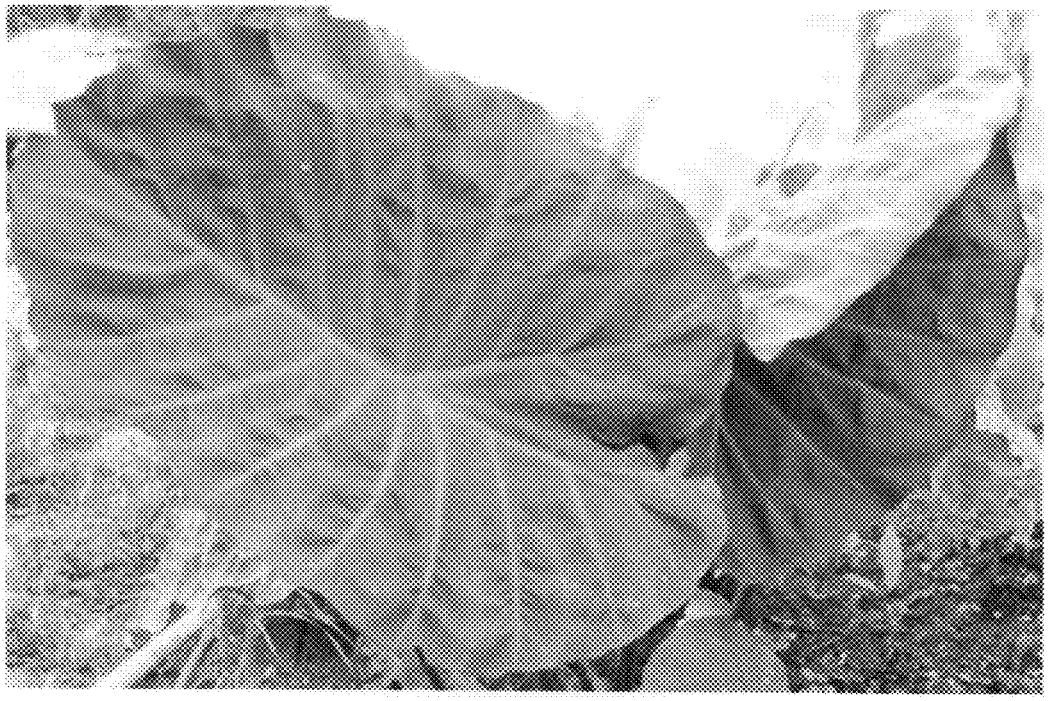

The photograph in FIG. 2 provides a close-up view of a younger leaf of 'Noble Gigante'.

Figure 3:
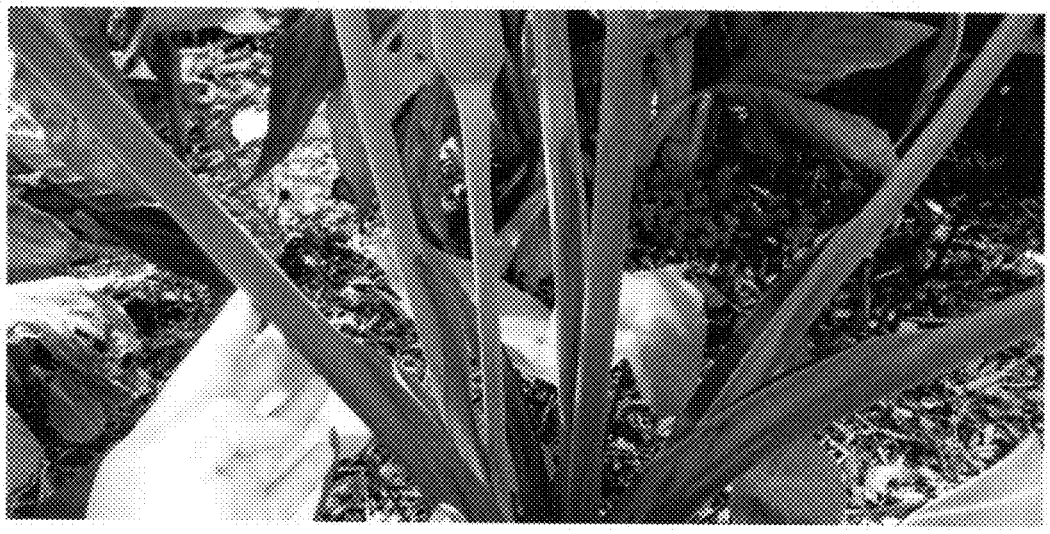

The photograph in FIG. 3 provides a view of the petioles and bloom stalks of 'Noble Gigante'.

The colors in the photographs are as close as possible with the photographic and printing technology utilized and the color values cited in the Detailed Botanical Description accurately describe the colors of the new *Colocasia*.

DETAILED BOTANICAL DESCRIPTION OF THE PLANT

The following is a detailed description of three year-old plants of the new cultivar as grown outdoors in full sun under 2 mm poly greenhouse plastic in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Mid summer until frost in Kentucky.

*Plant type*.—Tropical perennial herb.

*Plant habit*.—Upright, stemless.

*Propagation type*.—In vitro propagation is preferred.

*Growth rate*.—Vigorous.

*Stem description*.—Stemless.

Foliage description:

*Leaf shape*.—Ovate-slightly oblong.

*Leaf division*.—Single.

*Leaf base*.—Cordate.

*Leaf apex*.—Acute, slightly cuspidate.

*Leaf venation*.—Pinnate, color: upper young surface; 149A, upper mature surface; N187B, young lower surface; 145D, mature lower surface; a blend of 183A and 191A.

*Leaf margins*.—Undulate.

*Leaf attachment*.—Petiolate.

*Leaf arrangement*.—Alternate.

*Leaf surface*.—Upper surface and lower surface; coriaceous and glabrous and slightly pubescent.

*Leaf orientation*.—Held horizontal.

*Leaf color*.—Young foliage: upper surface; a blend of 137A and 138A, lower surface; 138B and lightly suffused with N77A, maturing foliage upper and lower surface becoming increasingly suffused with N77A, mature foliage upper and lower surface; N187A and blushed with N187B.

*Leaf size*.—Up to 1.2 m in length and 70 cm in width.

*Petioles*.—Held erect to semi-erect, an average of 1.2 m in length and 1.3 cm in distal diameter and 7.6 cm in proximal diameter, glaucous surface, N77C in color.

Inflorescence description:

*Inflorescence type*.—Spadix surrounded by a spathe.

*Inflorescence size*.—Average of 24 cm in length and 4 cm in diameter.

*Inflorescence bud*.—Lanceolate in shape with an inflated region near base, an average of 24 cm in length and 3 cm in width, a blend of N77B and N79A in color.

*Flower fragrance*.—None.

*Lastingness of inflorescence*.—Arise intermittently through bloom season, inflorescence last about 2 weeks.

*Inflorescence No.*—1 to 2 present at one time.

*Spathe*.—Hooded, bract, subtending spadix, lanceolate in shape with oblong base, entire margin, apiculate apex, coriaceous and glaucous on outer surface and glaucous and smooth on inner surface, 21 cm in length and 4 cm in width, lasts 5 to 7 days, color: when opening and fully open on surface; a blend of N77B and N79A, color: when opening and fully open on inner surface; a blend of a color between N77B and N79A and N155C.

*Spadix*.—Male portion above female zone with a sterile zone in the middle, upright cylindrical shape (phallus-like), apex narrowly pointed, about 1 cm in diameter (female portion 2 cm in diameter) and 17 cm in length, male zone; 1 cm in diameter and 8 cm in length, color immature and mature N77D with N77A between stamens, female zone; 2 cm in diameter and 2.5 cm in length, color immature and mature 144A with pistils 145C, flower quantity; an average of 200 female flowers and 400 male flowers, central sterile zone is an average of 4 cm in length, 1.2 cm in width and 157A in color.

*Peduncle*.—Emerges from base of plant, up to 30 cm in length and 1.4 cm in diameter, held upright, N79A in color, glaucous surface.

Reproductive organs:

*Gynoecium*.—Pistils are 144A in color, oblong in shape, 2 mm in height and 1.5 mm in width, stigmas are sessile on apex, about 0.5 mm in diameter and 157A in color, ovaries form a mass in center of stalk beneath pistils about 2.5 cm in length and 1.5 cm in width, NN155A in color.

*Androecium*.—Undeveloped, about 4 to 6 anther-like mounds per stamen, N77D in color with stamen about 1 mm in diameter.

*Fruit and seed*.—None were observed to form.

It is claimed:

1. A new and distinct cultivar of *Colocasia* plant named 'Noble Gigante' as herein illustrated and described.

* * * * *